(12) United States Patent
Pribanic

(10) Patent No.: US 9,320,507 B2
(45) Date of Patent: Apr. 26, 2016

(54) CANNULA VALVE ASSEMBLY

(71) Applicant: Covidien LP, Mansfield, MA (US)

(72) Inventor: Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 371 days.

(21) Appl. No.: 13/778,178

(22) Filed: Feb. 27, 2013

(65) Prior Publication Data

US 2013/0253280 A1    Sep. 26, 2013

Related U.S. Application Data

(60) Provisional application No. 61/615,515, filed on Mar. 26, 2012.

(51) Int. Cl.
*A61B 17/02* (2006.01)
*F16K 31/52* (2006.01)
*A61B 17/34* (2006.01)
*A61M 1/00* (2006.01)

(52) U.S. Cl.
CPC .......... *A61B 17/0218* (2013.01); *A61B 17/3421* (2013.01); *A61B 17/3423* (2013.01); *A61B 17/3474* (2013.01); *A61M 1/0039* (2013.01); *A61M 1/0084* (2013.01); *F16K 31/523* (2013.01)

(58) Field of Classification Search
CPC ........... A61B 17/0218; A61B 17/3421; A61B 17/3423; A61B 17/3474; A61M 13/003; A61M 1/0039; A61M 1/0084; A61M 1/0058; A61K 1/123; A61K 1/523; A61K 3/26; F16K 1/123; F16K 3/26; F16K 31/523
USPC ................. 606/108, 184, 185, 191, 167–172; 600/200–249, 159, 184; 604/165.01, 604/165.02, 167.03, 167.05, 167.01, 604/167.04, 167.02, 167.06, 264, 164.1, 604/164.01, 158; 251/344
See application file for complete search history.

(56) References Cited

U.S. PATENT DOCUMENTS

| | | | | |
|---|---|---|---|---|
| 3,395,705 A | * | 8/1968 | Hamilton | ............ A61M 1/0047 604/119 |
| 3,833,000 A | | 9/1974 | Bridgman | |
| 3,856,020 A | * | 12/1974 | Kovac | ...................... 604/170.03 |
| 3,859,985 A | * | 1/1975 | Eckhart | ................... A61B 6/504 137/625.17 |
| 4,280,498 A | * | 7/1981 | Jensen | ........................... 604/335 |

(Continued)

OTHER PUBLICATIONS

Extended European Search Report corresponding to EP 13 16 0791.3, completed Sep. 18, 2014 and mailed Sep. 26, 2014; (6 pp).

*Primary Examiner* — Todd E Manahan
*Assistant Examiner* — Marcela I Shirsat

(57) ABSTRACT

A surgical access device includes a housing member, a tubular member, a rotor and a lever. The housing member defines a lumen therethrough and includes a port in fluid communication with the lumen. The tubular member defines a longitudinal axis and a channel therethrough in fluid communication with the lumen of the housing member. The rotor defines a longitudinal passage therethrough and a bore on a sidewall of the rotor. The rotor is rotatably associated with the housing member and is coupled to the tubular member. The lever is translatably mounted on the housing member. Axial translation of the lever causes rotation of the rotor about the longitudinal axis between an open position in which the bore is aligned with the port providing a fluid communication between the port and the tubular member and a closed position in which the side wall of the rotor closes off the port.

18 Claims, 11 Drawing Sheets

(56) References Cited

U.S. PATENT DOCUMENTS

| | | | |
|---|---|---|---|
| 4,735,614 A * | 4/1988 | Yapp et al. | 604/165.01 |
| 4,775,365 A | 10/1988 | Swartz | |
| 4,784,649 A | 11/1988 | Imonti et al. | |
| 4,792,327 A | 12/1988 | Swartz | |
| 4,850,980 A | 7/1989 | Lentz et al. | |
| 4,924,851 A | 5/1990 | Ognier et al. | |
| 4,925,450 A | 5/1990 | Imonti et al. | |
| 4,943,280 A | 7/1990 | Lander | |
| 4,966,584 A | 10/1990 | Nguyen | |
| 5,013,300 A | 5/1991 | Williams | |
| 5,019,054 A | 5/1991 | Clement et al. | |
| 5,053,016 A | 10/1991 | Lander | |
| 5,083,743 A | 1/1992 | Gordon et al. | |
| 5,127,909 A | 7/1992 | Shichman | |
| 5,203,769 A | 4/1993 | Clement et al. | |
| 5,224,929 A | 7/1993 | Remiszewski | |
| 5,250,065 A | 10/1993 | Clement et al. | |
| 5,251,873 A | 10/1993 | Atkinson et al. | |
| 5,256,160 A | 10/1993 | Clement | |
| 5,269,768 A | 12/1993 | Cheung | |
| 5,306,237 A | 4/1994 | Clement et al. | |
| 5,312,351 A | 5/1994 | Gerrone | |
| 5,312,373 A | 5/1994 | Freitas | |
| 5,338,313 A | 8/1994 | Mollenauer et al. | |
| 5,360,413 A | 11/1994 | Leason et al. | |
| 5,370,624 A | 12/1994 | Edwards et al. | |
| 5,374,244 A | 12/1994 | Clement et al. | |
| 5,389,081 A | 2/1995 | Castro | |
| 5,391,154 A | 2/1995 | Young | |
| 5,399,167 A | 3/1995 | Deniega | |
| 5,413,309 A | 5/1995 | Giesler | |
| 5,458,640 A | 10/1995 | Gerrone | |
| 5,476,106 A | 12/1995 | Gartz | |
| 5,603,702 A | 2/1997 | Smith et al. | |
| 5,607,391 A | 3/1997 | Klinger et al. | |
| 5,647,845 A | 7/1997 | Haber et al. | |
| 5,709,664 A | 1/1998 | Vandenbroek et al. | |
| 5,725,374 A | 3/1998 | Young | |
| 5,755,686 A | 5/1998 | O'Neill et al. | |
| 5,792,112 A | 8/1998 | Hart et al. | |
| 5,807,338 A | 9/1998 | Smith et al. | |
| 5,865,812 A | 2/1999 | Correia | |
| 5,868,773 A | 2/1999 | Danks et al. | |
| 5,890,516 A * | 4/1999 | Talamonti | A61M 1/0047 137/605 |
| 5,902,264 A | 5/1999 | Toso et al. | |
| 6,083,203 A | 7/2000 | Yoon | |
| 6,093,176 A | 7/2000 | Dennis | |
| 6,099,505 A | 8/2000 | Ryan et al. | |
| 6,119,719 A * | 9/2000 | Viegener | 137/454.5 |
| 6,148,857 A | 11/2000 | West et al. | |
| 6,152,871 A | 11/2000 | Foley et al. | |
| 6,159,182 A | 12/2000 | Davis et al. | |
| 6,162,170 A | 12/2000 | Foley et al. | |
| 6,162,196 A | 12/2000 | Hart et al. | |
| 6,171,287 B1 | 1/2001 | Lynn et al. | |
| 6,197,007 B1 | 3/2001 | Thorne et al. | |
| 6,258,065 B1 | 7/2001 | Dennis et al. | |
| 6,273,861 B1 | 8/2001 | Bates et al. | |
| 6,293,952 B1 | 9/2001 | Brosens et al. | |
| 6,458,103 B1 | 10/2002 | Albert et al. | |
| 6,497,687 B1 | 12/2002 | Blanco | |
| 6,544,236 B1 | 4/2003 | Cragg et al. | |
| 6,569,119 B1 | 5/2003 | Haberland et al. | |
| 6,572,590 B1 | 6/2003 | Stevens et al. | |
| 6,623,445 B1 | 9/2003 | Nelson et al. | |
| 6,666,846 B1 | 12/2003 | Turovskiy et al. | |
| 6,689,146 B1 | 2/2004 | Himes | |
| 6,716,201 B2 | 4/2004 | Blanco | |
| 6,719,746 B2 | 4/2004 | Blanco | |
| 6,761,704 B2 | 7/2004 | Crawford | |
| 6,783,516 B2 | 8/2004 | O'Heeron et al. | |
| 6,855,128 B2 | 2/2005 | Swenson | |
| 6,883,778 B1 | 4/2005 | Newton et al. | |
| 6,964,658 B2 | 11/2005 | Ashby et al. | |
| 6,994,315 B2 | 2/2006 | Ryan et al. | |
| 7,008,412 B2 | 3/2006 | Maginot | |
| 7,033,339 B1 | 4/2006 | Lynn | |
| 7,044,936 B2 | 5/2006 | Harding et al. | |
| 7,172,572 B2 | 2/2007 | Diamond et al. | |
| 7,175,612 B2 | 2/2007 | Felix et al. | |
| 7,422,566 B2 | 9/2008 | Miethke | |
| 7,488,305 B2 | 2/2009 | Mickley et al. | |
| 7,494,481 B2 | 2/2009 | Moberg et al. | |
| 7,503,902 B2 | 3/2009 | Jensen et al. | |
| 7,520,489 B2 | 4/2009 | Ruschke et al. | |
| 7,559,530 B2 | 7/2009 | Korogi et al. | |
| 7,559,918 B2 | 7/2009 | Pasqualucci | |
| 7,585,288 B2 | 9/2009 | Haberland et al. | |
| 7,597,686 B2 | 10/2009 | MacMillan et al. | |
| 7,666,170 B2 | 2/2010 | Guala | |
| 8,070,730 B2 * | 12/2011 | Rockrohr | A61B 17/3474 604/167.01 |
| 2003/0047702 A1 * | 3/2003 | Gunnarsson | E21B 34/14 251/297 |
| 2003/0181850 A1 | 9/2003 | Diamond et al. | |
| 2003/0208165 A1 | 11/2003 | Christensen et al. | |
| 2005/0043690 A1 | 2/2005 | Todd | |
| 2006/0129112 A1 | 6/2006 | Lynn | |
| 2006/0135972 A1 | 6/2006 | Zeiner | |
| 2006/0229499 A1 | 10/2006 | Eisenkolb et al. | |
| 2007/0239108 A1 | 10/2007 | Albrecht et al. | |
| 2008/0108956 A1 | 5/2008 | Lynn et al. | |
| 2008/0132847 A1 | 6/2008 | Wing et al. | |
| 2008/0172003 A1 | 7/2008 | Plishka et al. | |
| 2008/0214993 A1 | 9/2008 | Haarala et al. | |
| 2009/0005740 A1 | 1/2009 | Smith | |
| 2009/0048609 A1 | 2/2009 | Atiomo et al. | |
| 2009/0082720 A1 | 3/2009 | Smith | |
| 2009/0275901 A1 * | 11/2009 | Mckinnon | 604/248 |
| 2011/0087169 A1 * | 4/2011 | Parihar | A61B 17/34 604/167.03 |

* cited by examiner

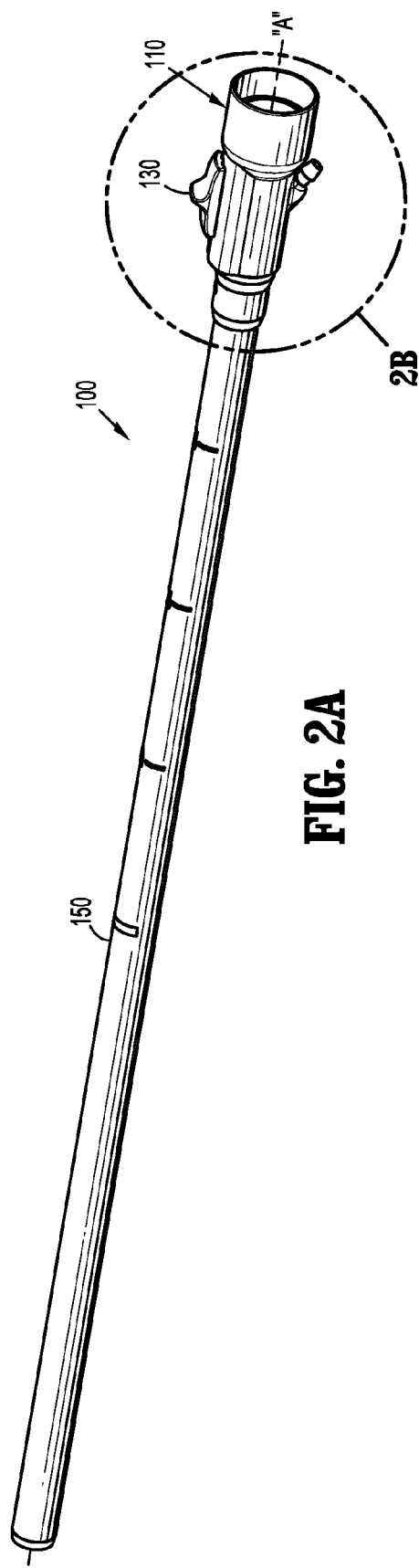
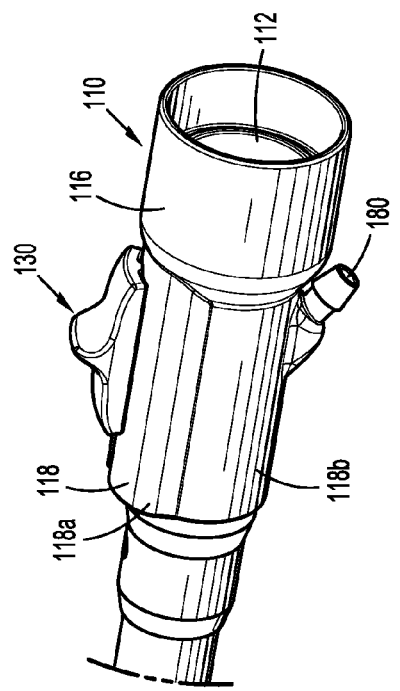
FIG. 2A
FIG. 2B

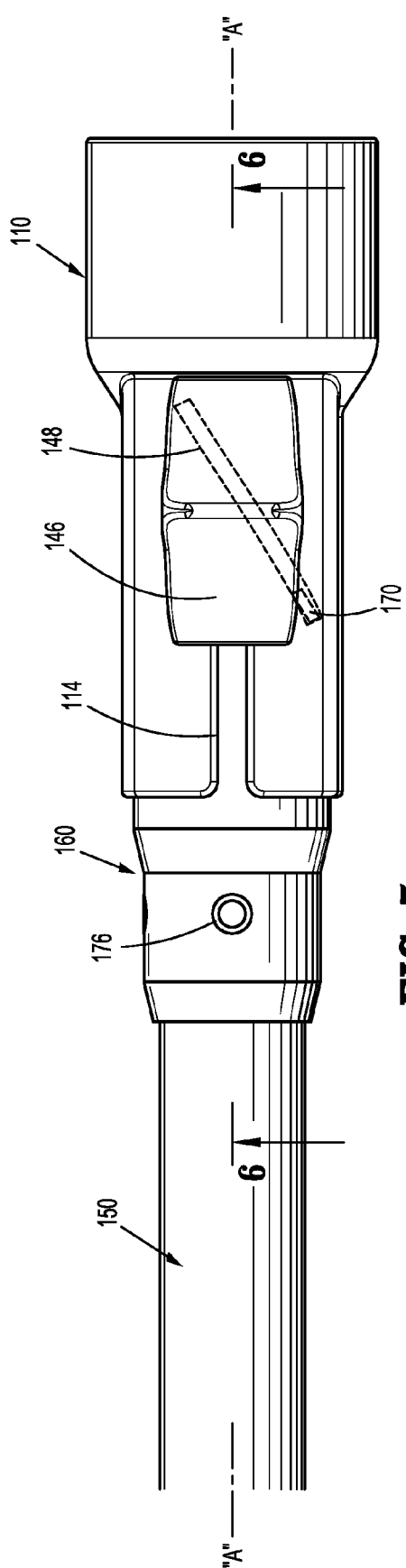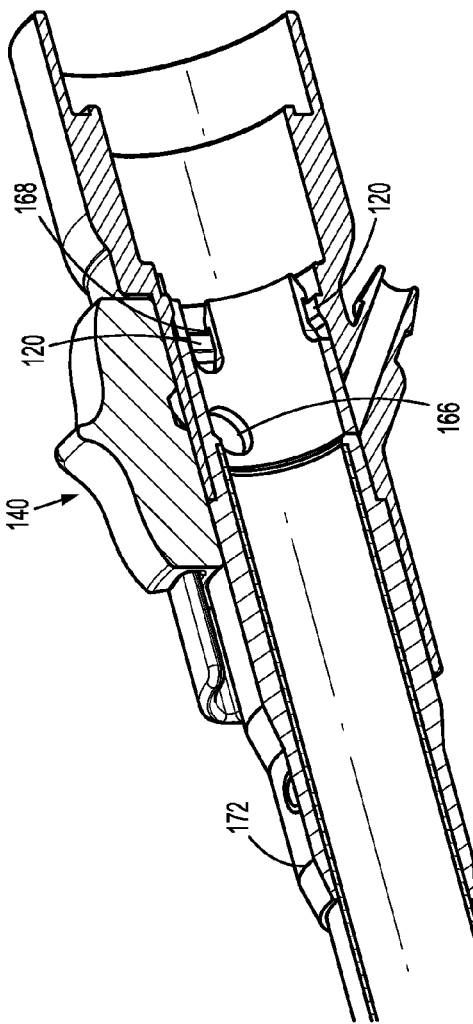
FIG. 5
FIG. 6

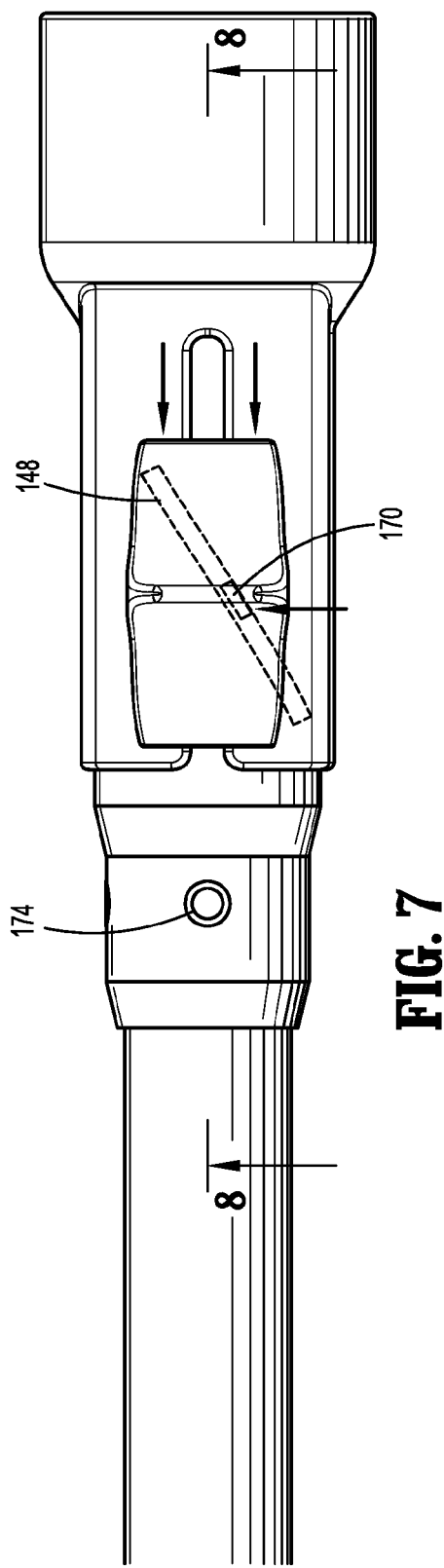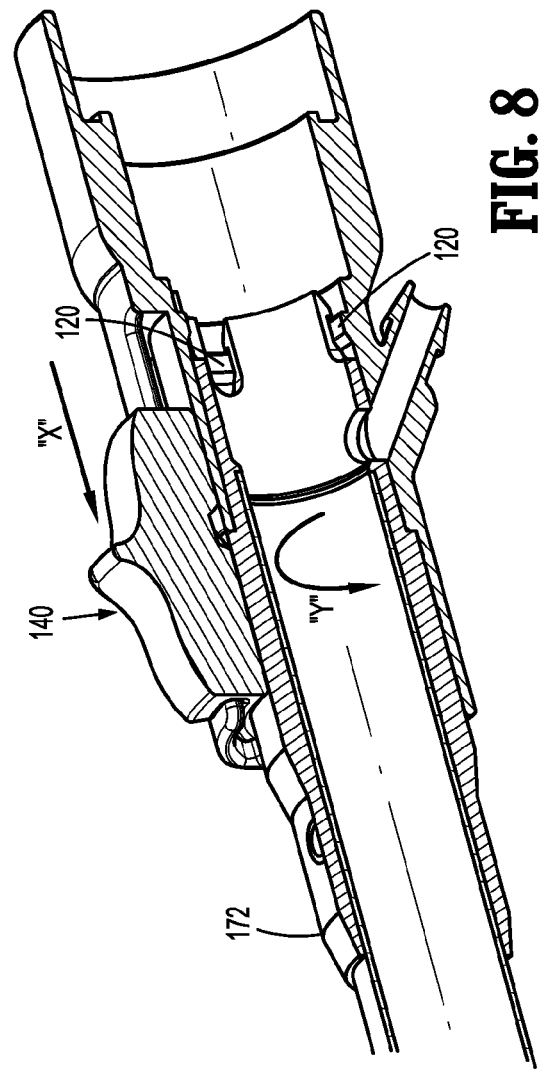

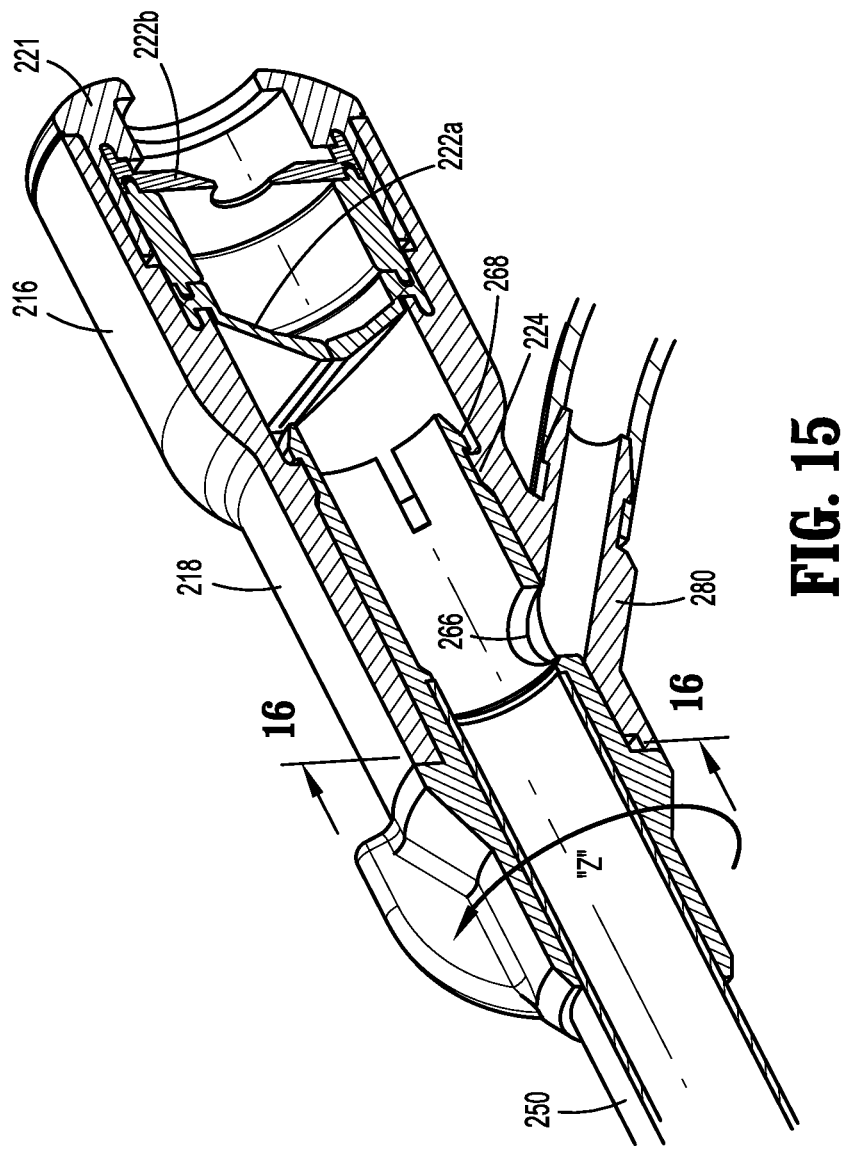
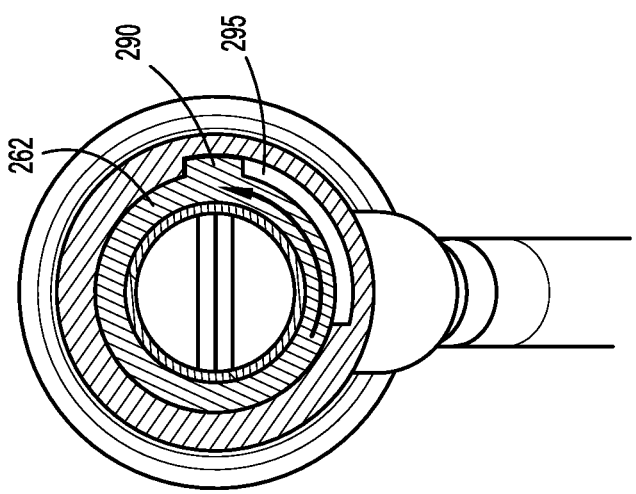
FIG. 15
FIG. 16

CANNULA VALVE ASSEMBLY

CROSS REFERENCE TO RELATED APPLICATION

The present application claims the benefit of and priority to U.S. Provisional Application Ser. No. 61/615,515, filed on Mar. 26, 2012, the entire contents of which are incorporated herein by reference

BACKGROUND

1. Technical Field

The present disclosure relates to a surgical access device, and more particularly, to a cannula including a single hand actuation valve assembly.

2. Background of Related Art

In laparoscopic and endoscopic surgical procedures, a small incision or puncture is made in a patient's body, e.g., in the abdomen, to provide an entry point for a surgical access device which is inserted into the incision and facilitates the insertion of instruments used in performing surgical procedures. When compared to the larger incisions typically found in traditional procedures, both trauma to the patient and recovery time are reduced for procedures involving small incisions. Due to the relatively small interior dimensions of the access devices used in endoscopic procedures, only the elongated, small diametered instrumentation may be used to access the internal body cavities and organs.

For example, a cannula is utilized to provide an access port for surgical instruments and a conduit for introducing insufflation fluids into the body cavity. Typically, a trocar is positioned within the cannula. The trocar pierces tissue creating the incision and separates tissue allowing the cannula to be advanced toward the surgical site. Upon placing the cannula at the desired surgical site, the trocar is removed leaving the cannula in place. Thereafter, insufflation fluid (e.g. carbon dioxide) is introduced into the body cavity to enlarge the area surrounding the target surgical site to create an accessible work area, prior to the introduction of the surgical instruments into the patient's body. The surgeon is then able to perform the procedure within the abdominal cavity by manipulating the instruments that have been extended through the access assemblies. The manipulation of such instruments within the internal body is similarly limited by both spatial constraints and the need to maintain the body cavity in an insufflated state.

Accordingly, there is a need for an access device having an easily operable valve assembly while the surgeon uses various instrumentations during the surgical procedure, in order to maintain the enlarged surgical site.

SUMMARY

In accordance with the present disclosure, there is provided a surgical access device including a housing member, a tubular member, a rotor and a lever. The housing member defines a lumen therethrough and includes a port in fluid communication with the lumen. The tubular member defines a channel therethrough in fluid communication with the lumen of the housing member. The tubular member defines a longitudinal axis. The rotor defines a longitudinal passage therethrough and a bore on a sidewall of the rotor. The rotor is rotatably associated with the housing member and is coupled to the tubular member. The lever is translatably mounted on the housing member. Axial translation of the lever causes rotation of the rotor about the longitudinal axis between an open position in which the bore is aligned with the port providing a fluid communication between the port and the tubular member and a closed position in which the side wall of the rotor closes off the port. In addition, the rotor may be rotated to an intermediate position in which the bore is partially aligned with the port providing a fluid communication between the port and the tubular member.

In another embodiment, the lever may include first and second members in a substantially superposed relation with each other. The first member may be slidably disposed on an outer surface of the housing and the second member may be slidably disposed on an inner surface of the housing.

In still another embodiment, an inner surface of the second member of the lever may define a groove along a length thereof. The rotor may include a nub radially extending from the side wall of the rotor. The nub may slidably engage the groove defined in the second member.

In still another embodiment, the groove may define an acute angle with respect to the longitudinal axis. The nub of the rotor may be oriented at an angle with respect to the longitudinal axis.

In yet another embodiment, the housing member may include a circumferential ridge radially extending from the inner surface thereof. The rotor may define a circumferential groove corresponding to the circumferential ridge of the housing member. The circumferential groove may rotatably engage the circumferential ridge.

In still another embodiment, the first member of the lever may conform to a contour of the outer surface of the housing member. The second member of the lever may conform to a contour of an outer surface of the rotor.

In still yet another embodiment, the port may be connected to at least one of a fluid supply or a vacuum source.

In accordance with another embodiment of the present disclosure, there is provided a surgical access device including a cannula including a housing and a tubular member extending from the housing and a rotatable hub defining a passage therethrough. The housing includes a port in communication with the tubular member. The rotatable hub includes a first portion rotatably disposed within the housing and defining a bore and a second portion at least partially surrounding the tubular member. Rotation of the second portion causes concomitant rotation to the first portion between an open position in which the bore is aligned with the port providing a fluid communication between the port and the tubular member and a closed position in which the first portion closes off the port.

In another embodiment, the rotatable hub may include a nub radially extending from an outer surface of the rotatable hub. The housing may define a partially circumferential groove. The nub may slidably engage the partially circumferential groove. The partially circumferential groove may define a 90-degree angle.

In still another embodiment, the first portion of the rotatable hub may define a circumferential groove. The housing may include a circumferential ridge radially extending from an inner surface of the housing. The circumferential groove of rotatable hub may rotatably engage the circumferential ridge of the housing.

In still yet another embodiment, the port may be connected to at least one of a fluid supply or a vacuum source.

BRIEF DESCRIPTION OF THE DRAWINGS

Various embodiments of the present disclosure are described hereinbelow with reference to the drawings, wherein:

FIG. 2A is a perspective view of a surgical access device including a single hand actuation valve assembly in accordance with an embodiment of the present disclosure;

FIG. 2B is a perspective view of the area of detail indicated in FIG. 2A;

FIG. 5 is a partial longitudinal top view of the surgical access device of FIG. 2A illustrating the valve assembly in a closed state;

FIG. 6 is a partial cross-sectional view taken along section line 6-6 of FIG. 5;

FIG. 7 is a partial longitudinal top view of the surgical access device of FIG. 2A illustrating the valve assembly in an open state;

FIG. 8 is a partial cross-sectional view taken along section line 8-8 of FIG. 7;

FIG. 15 is a partial cross-sectional view of the surgical access device of FIG. 9 illustrating the valve assembly in an open state; and FIG. 16 is a cross-sectional view taken along section line 16-16 of FIG. 15.

DETAILED DESCRIPTION OF EMBODIMENTS

Figure 1:
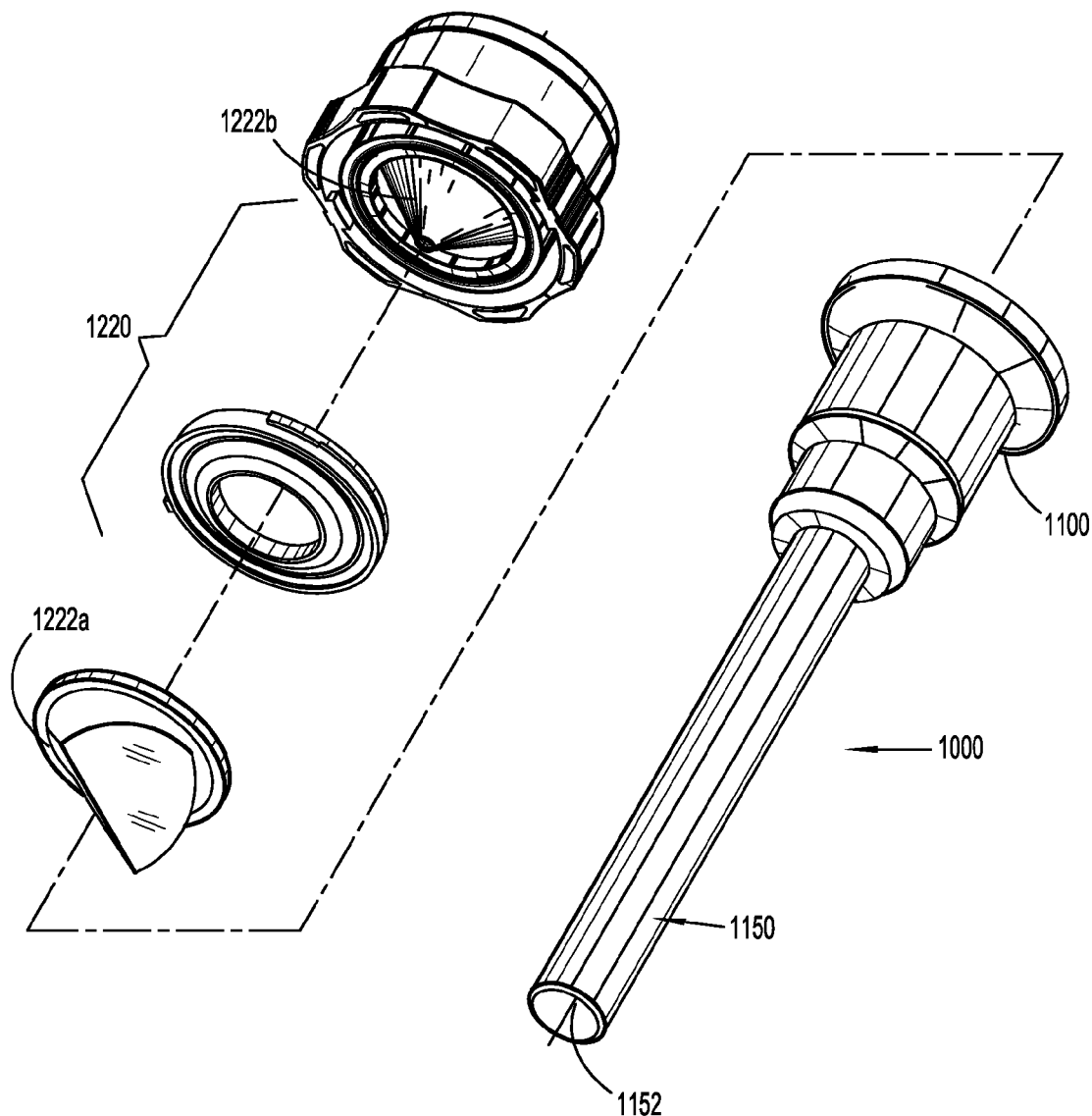
FIG. 1 is an exploded perspective view of a prior art surgical access device with parts separated.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, a prior art surgical access device 1000 is illustrated. Access device 1000 is adapted for insertion within a tissue tract, e.g., through the abdominal or peritoneal lining, in connection with a laparoscopic or endoscopic surgical procedure. Access device 1000 includes a housing 1100 and a tubular member 1150 extending longitudinally from housing 1100. Housing 1100 defines a lumen (not shown) in communication with a longitudinal passage 1152 defined in tubular member 1150. Surgical instruments or an endoscope (not shown) may be received through the lumen of housing 1100 and longitudinal passage 1152 of tubular member 1150. Furthermore, tubular member 1150 may be flexible to conform to a curve or bend in a surgical instrument inserted therethrough. Housing 1100 may include an insufflation port (not shown) for introduction and/or discharge of insufflation gases through longitudinal passage 1152 of access device 1000. In addition, access device 1000 may further include a seal assembly 1220 adapted to form or establish a sealing relation with a surgical instrument introduced through access device 1000. For example, seal assembly 1220 may include a pair of seals 1222a, 1222b fabricated from a suitable elastomeric material, gel material, foam material or a fluid filled cavity having sufficient compliance to form a seal about the surgical instrument. Seal assembly 1220 may be mounted on housing 1100.

In addition, surgical access device 1000 may further include a balloon dissector (not shown) slidably mounted therethrough. The balloon dissector includes an inflatable dissection balloon that may be inflated in tissue to cause tissue to separate along a natural plane, providing a more accessible operating space.

With reference now to FIGS. 2A and 2B, an embodiment of the present disclosure is shown generally as a cannula 100 defining a longitudinal axis "A-A." Cannula 100 includes a housing portion 110, a tubular member 150 extending distally from housing member 110 and a valve assembly 130. Housing portion 110 defines a lumen 112 in communication with a longitudinal channel 152 (FIG. 3) defined in tubular member 150. Surgical instruments or an endoscope may be received through lumen 112 and longitudinal channel 152. Furthermore, tubular member 150 may be flexible to conform to a curve or bend in a surgical instrument inserted therethrough. More importantly, the flexibility allows the cannula to adapt to the working space.

With particular reference to FIG. 2B, housing portion 110 includes a port 180, a head portion 116 and a neck portion 118 extending distally from head portion 116. Head portion 116 has a diameter greater than that of neck portion 118 to facilitate insertion of the surgical instruments therethrough. Port 180 is disposed on neck portion 118 and may be utilized to provide insufflation gas to the body cavity through longitudinal channel 152 of tubular member 150. Alternatively, port 180 may also be utilized as a suction port that is connected to a vacuum source 400 (FIG. 9) to provide suction at the surgical site.

Figure 3:
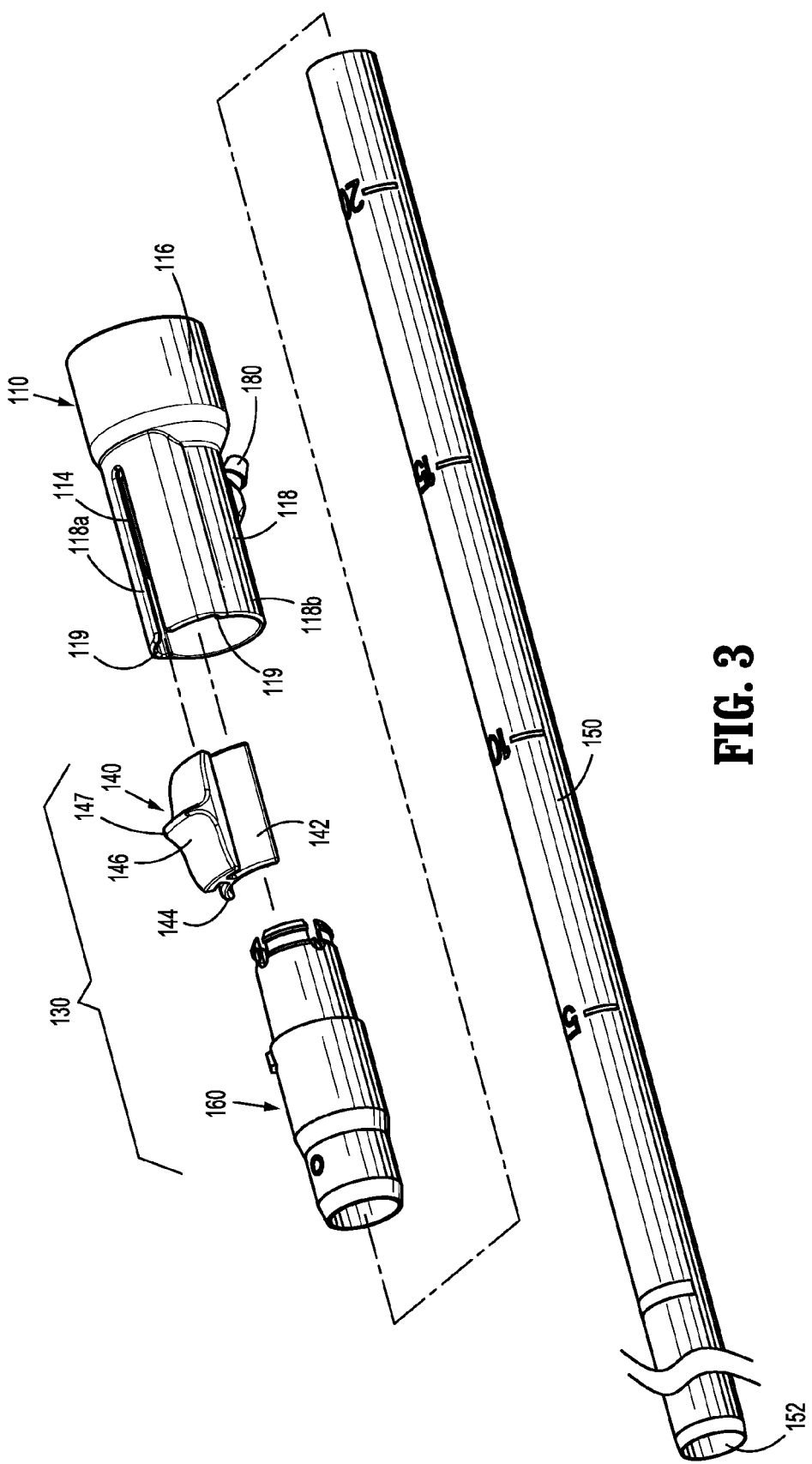
FIG. 3 is an exploded perspective view of the surgical access device of FIG. 2A with parts separated.

With reference now to FIG. 3, neck portion 118 includes a receiving portion 118a including a pair of opposing slots 119 and a body portion 118b having a partially circular cross section. Receiving portion 118a defines a slit 114 extending at least partially along a length thereof. In addition, neck portion 118 includes a circumferential ridge 120 (FIG. 6) extending radially inward from an inner surface of neck portion 118, as best shown in FIG. 8.

Figure 4:
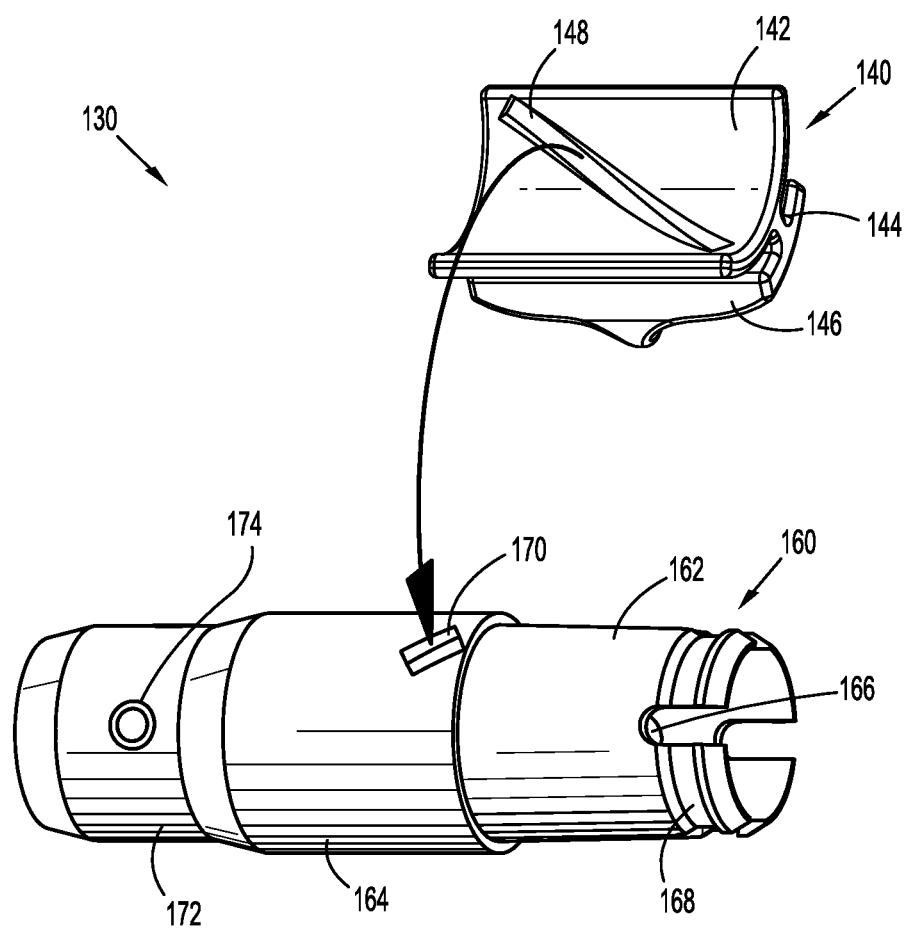
FIG. 4 is a perspective view of the single hand actuation valve assembly of FIG. 2A with parts separated.

With reference now to FIGS. 3 and 4, valve assembly 130 includes a sliding lever 140 and a rotor 160. Sliding lever 140 is translatably mounted on neck portion 118 of housing portion 110, and rotor 160 is rotatably coupled to neck portion 118. In particular, sliding lever 140 includes a guide portion 142, a slider member 146 and a connector 144. Guide portion 142, connector 144 and slider member 146 may be molded from a relatively rigid material such as, polycarbonate plastic and may be monolithically formed. Guide portion 142 and slider member 146 are opposingly coupled by connector 144 in a substantially superposed relation therewith, whereby sliding lever 140 has a substantially I-shaped cross-section. Connector 144 is translatably disposed within slit 114 defined in neck portion 118 of housing portion 110, such that guide portion 142 is at least partially slidably disposed within slots 119 of receiving portion 118a of neck portion 118 and slider member 146 is translatably disposed on an outer surface of receiving portion 118a. In particular, slider member 146 is configured to at least partially conform to the contour of the outer surface of receiving portion 118a, and guide portion 142 is configured to at least partially conform to the contour of the inner surface of neck portion 118 and axially translate in the pair of slots 119. Guide portion 142 and body portion 118b substantially define a circular cross-section. In this manner, axial translation of slider member 146 causes translation of guide portion 142 in slots 119. In addition, slider member 146 may include a ridge 147 oriented substantially orthogonal to direction of travel to facilitate actuation of slider member 146 by, for example, a thumb. Guide portion 142 defines a cam slot 148 on an inner surface thereof. In particular, cam slot 148 may define, for example, an acute angle with respect to longitudinal axis "A-A," as shown in FIG. 4.

With continued reference to FIGS. 3 and 4, rotor 160 is rotatably associated with housing portion 110 and tubular member 150. In particular, rotor 160 includes a securing portion 162 and an engaging portion 164. Securing portion 162 has a smaller diameter than that of engaging portion 164. Securing portion 162 defines a bore 166 on a side wall thereof and a circumferential recess 168 adjacent a proximal end portion of rotor 160. Circumferential recess 168 rotatably engages circumferential ridge 120 of neck portion 118, as shown in FIG. 6. In this manner, rotor 160 may be rotatably associated with housing portion 110 without relative axial movement between rotor 160 and housing portion 110.

With continued reference to FIGS. 4-6, rotor 160 is at least partially disposed within housing portion 110, and tubular member 150 is at least partially secured within rotor 160. In particular, engaging portion 164 of rotor 160 extends distally from securing portion 162. Engaging portion 164 includes a tapered portion 172 that surrounds at least a portion of tubular member 150. In addition, engaging portion 164 includes a nub 170 on an outer surface thereof. Nub 170 slidably engages cam slot 148 defined in the inner surface of guide portion 142 of sliding lever 140, as shown in phantom in FIG. 5. As discussed hereinabove, cam slot 148 defines, for example, an acute angle, with respect to longitudinal axis "A-A." As such, axial translation of sliding lever 140 along longitudinal slit 114 causes rotation of rotor 160 about longitudinal axis "A-A" without relative axial movement between rotor 160 and housing portion 110. In this manner, bore 166 defined in the side wall of securing portion 162 of rotor 160 may be rotatably aligned with port 180 on housing portion 110 to provide fluid communication with port 180. Furthermore, rotor 160 may be rotatably misaligned with port 180 to close off port 180. For example, cam slot 148 defined in the inner surface of guide portion 142 and bore 166 defined in rotor 160 can be configured to align with port 180 when slider member 146 is translated to a distal-most position along longitudinal slit 114, as shown in FIGS. 7 and 8. As such, when slider member 146 is disposed at any other position along longitudinal slit 114, bore 166 is misaligned with port 180, thereby closing off fluid communication therebetween. For example, when slider member 146 is at a proximal-most position, as shown in FIG. 5, bore 166 diametrically opposes port 180 and closes off fluid communication therebetween. By selectively choosing the proximal-most position of slider member 146 along longitudinal slit 114 as a shut-off position and the distal-most position of slider member 146 as an open position, the user may readily determine whether bore 166 is in communication with port 180. However, it is contemplated that visual indicia 174, 176 may be provided on an outer surface of engaging portion 164, such as those shown in FIGS. 4 and 5. For example, when slider member 146 is in the distal-most position, thereby establishing a fluid communication between bore 166 and port 180, an open circle 174, 176 is shown. However, when in the proximal-most position, a filled circle 176 is shown to indicate that rotor 160 has closed-off fluid communication between bore 166 and port 180. It is further contemplated that rotor 160 may be rotated to an intermediate position in which bore 166 is partially aligned with port 180 providing a fluid communication between port 180 and tubular member 150.

A user may securely hold housing portion 110 and actuate sliding lever 140 with, for example, the thumb, of the hand that is holding housing portion 110, without having to use the other hand. It is envisioned that housing portion 110 may define, for example, transversely recessed portions for gripping comfort and placement of the fingers. Furthermore, sliding lever 140 and port 180 may diametrically oppose each other such that port 180 including, for example, fluid supply tubes, do not interfere with the axial translation of slider member 146.

It is further contemplated that securing portion 162 of rotor 60 may define additional bores (not shown) to reduce the distance of travel by slider member 146 to establish fluid communication between bore 166 and port 180. For example, the additional bore may be configured to establish fluid communication between the bore and port 180 when slider member 146 is disposed at, for example, a midpoint between the proximal-most position and the distal-most position along slit 114. Furthermore, slit 114 may provide a detent mechanism or tactile means (not shown) to indicate to the user the intermediate positions between the proximal-most and distal-most positions in which the additional bores are aligned with port 180, thereby providing fluid communication therewith. It is further envisioned that securing portion 162 of rotor 160 may define additional bores having various diameters. In this manner, the user may control the fluid flow and fluid pressure by choosing the desired fluid flow and/or pressure associated with the bore. In addition, by arranging bores with various sizes in diameter, the user can gradually increase or decrease the fluid flow and fluid pressure in the body cavity. For example, when slider member 146 is at the proximal-most position along longitudinal slit 114, securing portion 162 of rotor 160 blocks fluid communication between port 180 and tubular member 150, as described hereinabove. However, as slider member 146 is translated distally a predetermined amount, a bore having the smallest diameter aligns with port 180 providing fluid communication with port 180. As slider member 146 is translated farther distally for a predetermined amount, a bore with a larger diameter is aligned with port 180. The diameter of bores gradually increases until bore 166 has a diameter equivalent to that of port 180. As such, as slider member 146 reaches a distal-most position along longitudinal slit 114, port 180 aligns with the bore having the radius equivalent to that of port 180. The number of bores and the variation in the sizes of the diameter of the bores may be tailored to the application being performed. In this manner, the user may control the flow and pressure of the fluid, as well as establishing or cutting off fluid communication by a single hand. In addition, the snug fit of rotor 160 and the type of material chosen for rotor 160 may also affect the pressure capacity of valve assembly 130. It is also envisioned that the bores with various sizes in diameter may be communicated to provide a continuous flow of the fluid through the bores during adjustments or movement of slider member 146.

It is further contemplated that head portion 116 of housing portion 110 may include a seal assembly (not shown) adapted to form or establish a sealing relation with a surgical instrument introduced through lumen 112. For example, the seal may be fabricated from a suitable elastomeric material, gel material, foam material or a fluid filled cavity having sufficient compliance to form a seal about the surgical instrument. In addition, cannula 100 may further include a collar (not shown) surrounding at least partially tubular member 150. The collar may be made from a compressible and/or flexible type material having sufficient compliance to form a sealing relationship with the incision site and to accommodate off-axis motion of tubular member 150 during a surgical procedure.

In use, cannula 100 is inserted through a small incision made in the skin of a patient, e.g., in the abdominal cavity wall, or through a natural orifice. Upon placement of a distal end of cannula 100 adjacent the target surgical site, a fluid supply may be connected to port 180. Optionally, an obturator may be utilized to advance cannula 100 into the tissue and an inflatable dissection balloon may be used to dissect tissue to provide working space. Thereafter, slider member 146 may be actuated, to align bore 166 with port 180 to provide fluid communication therebetween. In this manner, insufflation fluid, for example, may be supplied to the body cavity to maintain accessible working space as desired. Surgical instruments may then be inserted through lumen 112 and longitudinal channel 152 of cannula 110 while maintaining a sealing relationship with the seal. Cannula 100 enables the user to conveniently control the supply of fluid, as well as gripping housing portion 110, by a single hand. In addition, by utilizing bores of various sizes in diameter, the user may control the flow and pressure of the fluid that is supplied to the body cavity. Optionally, the collar may be used to seal the incision and to anchor tubular member 150 to the body.

Figures 9, 10:
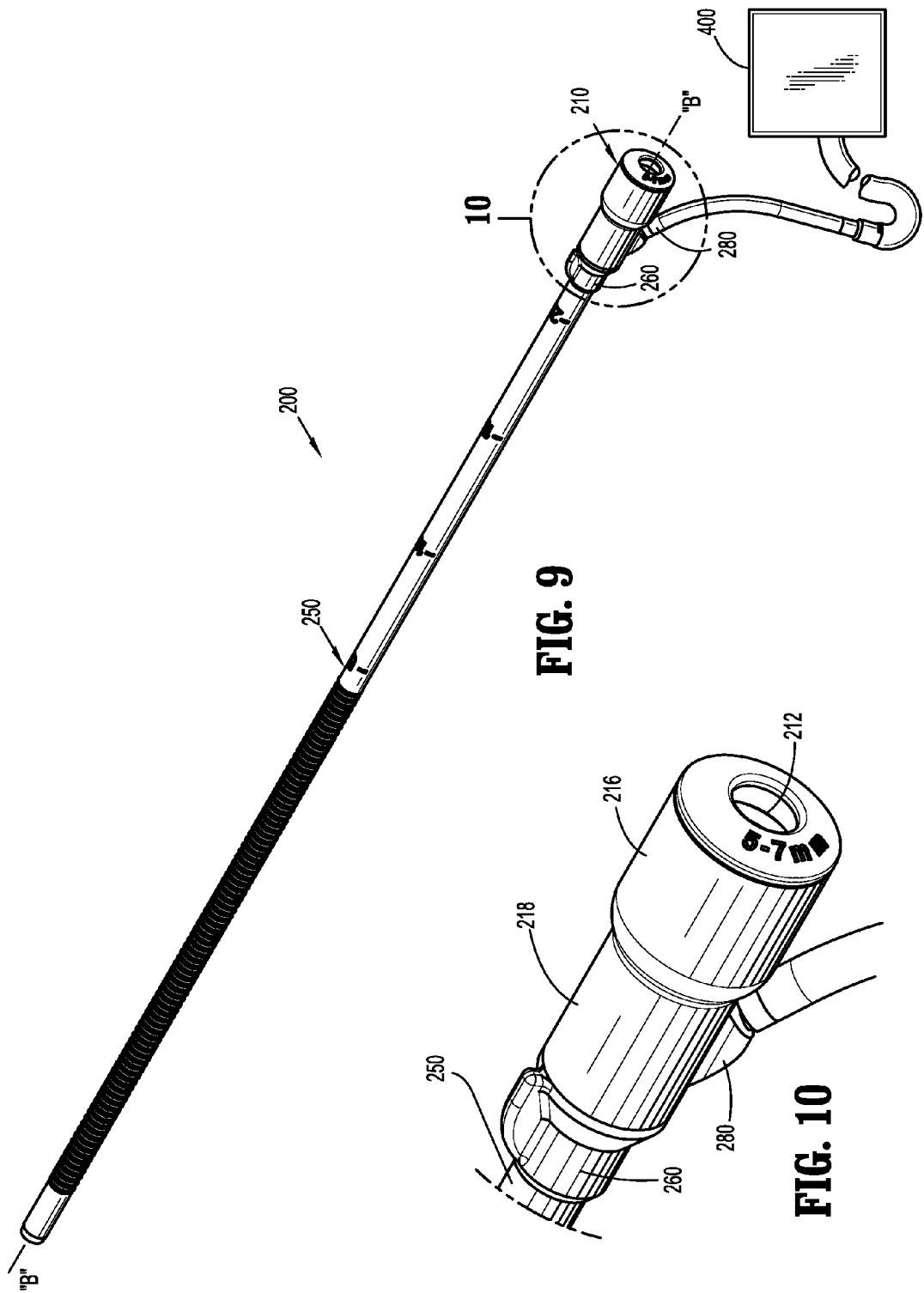
FIG. 9 is a perspective view of a surgical access device including a single hand actuation valve in accordance with another embodiment of the present disclosure.
FIG. 10 is a perspective view of the area of detail indicated in FIG. 9.

With reference now to FIGS. 9 and 10, a cannula in accordance with another embodiment of the present disclosure is shown generally as 200. Cannula 200 is substantially similar to cannula 100, and thus will only be described herein to the extent necessary to identify differences in construction and operation thereof. Throughout the following disclosure, like reference numerals will be used to identify like elements.

Figure 11:
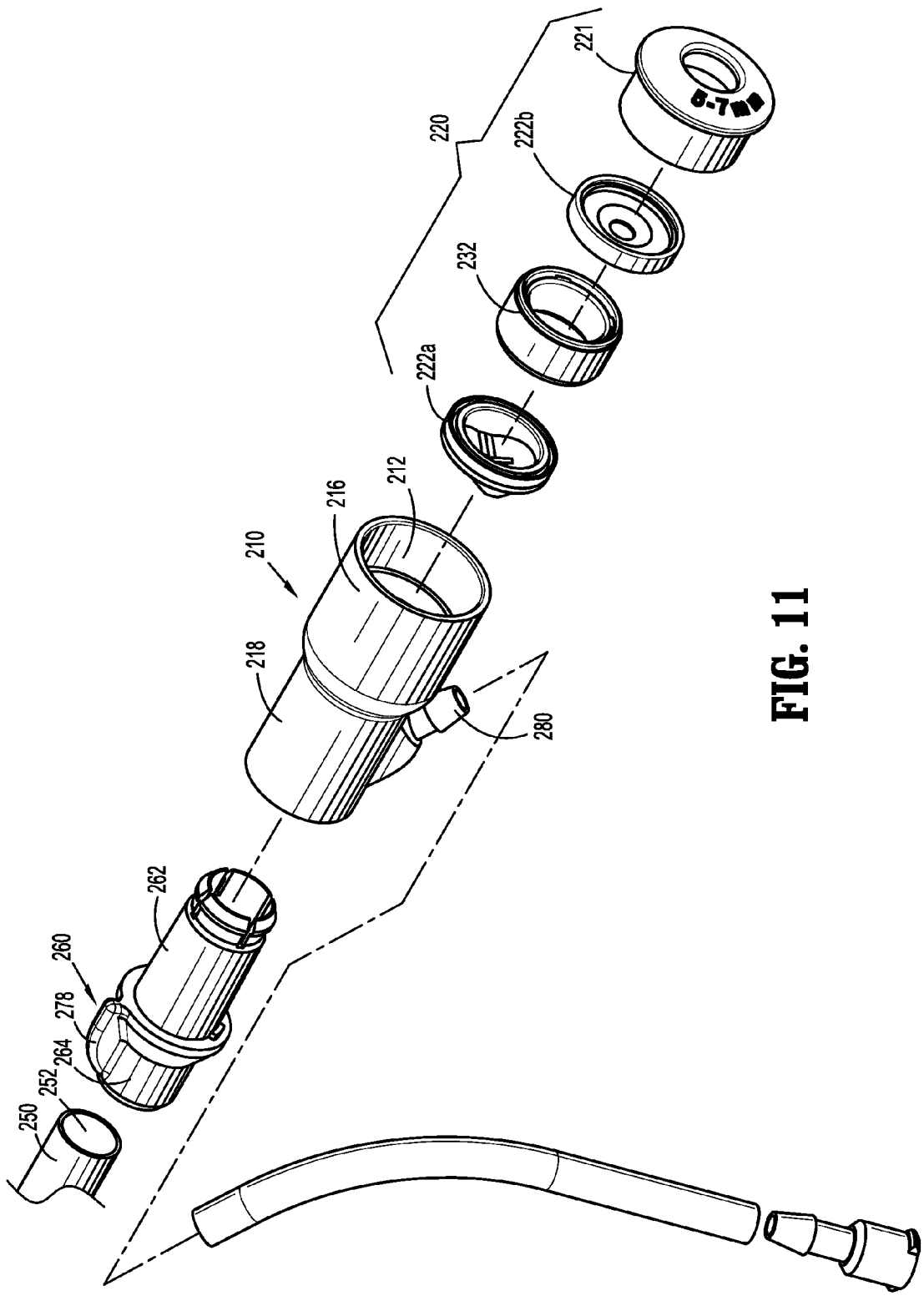
FIG. 11 is an exploded perspective view of the surgical access device of FIG. 9 with parts separated.
Figure 12:
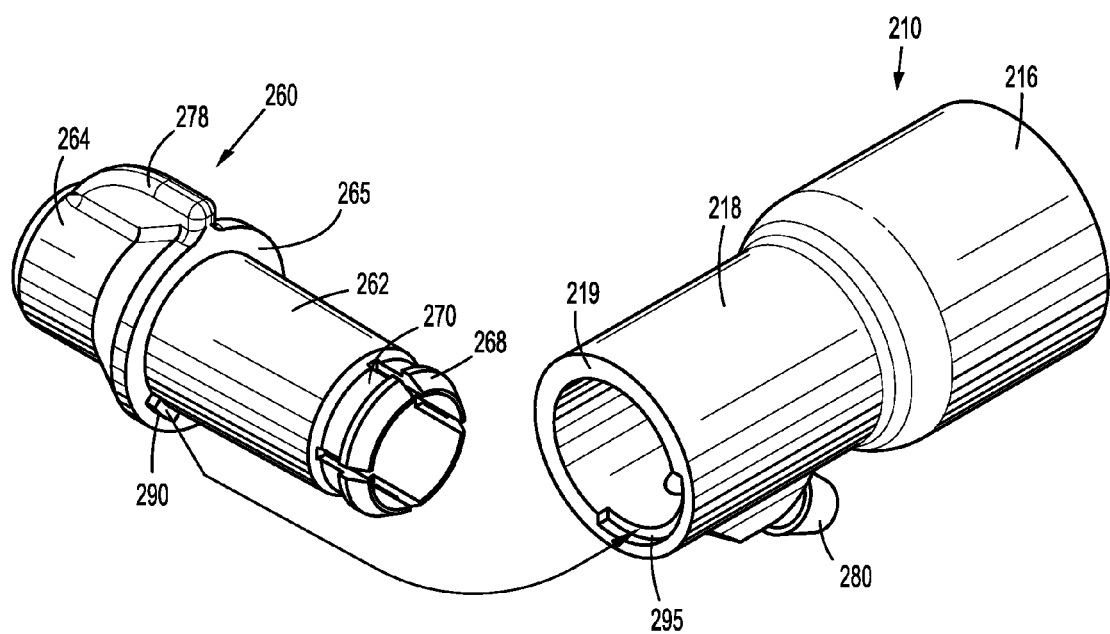
FIG. 12 is a perspective view of the single hand actuation valve assembly of FIG. 9 with parts separated.
Figure 13:
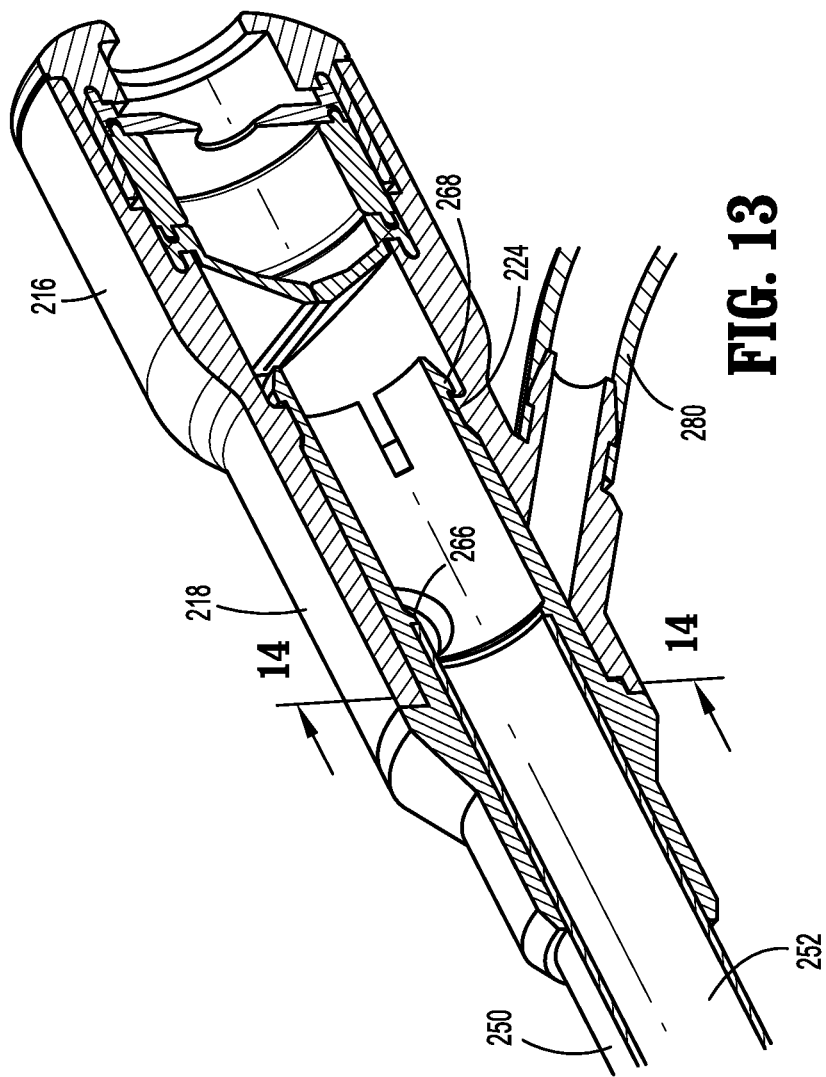
FIG. 13 is a partial cross-sectional view of the surgical access device of FIG. 9 illustrating the valve assembly in a closed state.

With particular reference to FIGS. 10 and 11, cannula 200 includes a housing portion 210, a tubular member 250 extending distally from housing member 210 and a rotor 260. Housing portion 210 includes a port 280, a head portion 216 and a neck portion 218 extending distally from head portion 216. Head portion 216 has a diameter greater than that of neck portion 218. Port 280 is disposed on neck portion 218 and may be connected to a fluid source 400, as shown in FIG. 9. Fluid source 400 may supply fluids (e.g. gas or liquid) under pressure and/or vacuum to port 280. In particular, port 280 may be utilized to provide insufflation gas, as well as suction, to the body cavity through longitudinal channel 252 of tubular member 250. In particular, neck portion 218 includes a circumferential ridge 224 extending radially inward, as shown in FIG. 13, and a partially circumferential groove 295 defined in a distal end portion of neck portion 218, as shown in FIG. 12. Groove 295 is configured to enable only a partial rotation of rotor 260, as will be discussed in detail below.

With particular reference to FIG. 11, housing portion 210 defines a lumen 212 in communication with a longitudinal channel 252 defined in tubular member 250. Surgical instruments or an endoscope may be received through lumen 212 and longitudinal channel 252. Housing portion 210 includes a seal assembly 220 that includes a pair of seals 222*a*, 222*b* mounted within lumen 212 to establish a sealing relation with a surgical instrument introduced through cannula 200. In particular, seals 222*a*, 222*b* are separated by a mount 232 and are secure to housing portion 210 by an end cap 221, which substantially covers a proximal opening of housing portion 210. Seals 222*a*, 222*b* may be made from a suitable material having sufficient compliance to form a seal about the surgical instrument.

With reference now to FIGS. 12 and 13, rotor 260 is rotatably secured to housing portion 210 and tubular member 250. Rotor 260 includes a first portion 262 and a second portion 264. First portion 262 has a smaller diameter than that of second portion 264. First portion 262 defines a bore 266 and a circumferential recess 270. In addition, first portion 262 includes a circumferential finger 268 radially extending outward and proximal of circumferential recess 270. First portion 262 of rotor 260 is rotatably disposed within neck portion 218. Specifically, circumferential ridge 224 of neck portion 218 rotatably engages circumferential recess 270 of first portion 262. Furthermore, circumferential finger 268 engages proximal end portion of circumferential ridge 224 of neck portion 218, which inhibits axial translation of rotor 260 within lumen 212.

With continued reference to FIG. 12, rotor 260 further includes a nub 290 that radially extends from a proximal end portion of first portion 262. Nub 290 slidably engages groove 295 defined in an inner surface of neck portion 218. Rotor 260 is at least partially disposed within housing portion 210, and tubular member 250 is at least partially secured within rotor 260.

Second portion 264 extends distally from first portion 262 and surrounds at least a portion of tubular member 250. In particular, second portion 264 is substantially coterminous with an outer surface of neck portion 218. In this manner, rotor 260 is rotatably secured with housing portion 210 without relative axial movement with respect to housing portion 210, as circumferential finger 268 and outer portion 264 each restrict distal and proximal movement of rotor 260, respectively.

Figure 14:
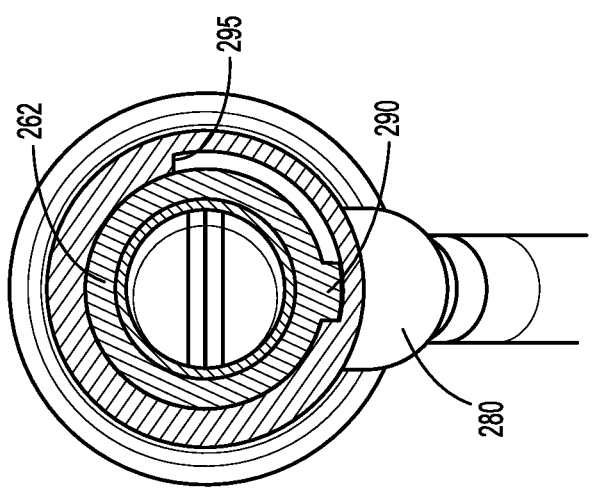
FIG. 14 is a cross-sectional view taken along section line 14-14 of FIG. 13.

In particular, second portion 264 includes a longitudinal member 278 aligned with a longitudinal axis "B-B," defined by cannula 200. Rotation of longitudinal member 278 about longitudinal axis "B-B" causes concomitant rotation of first portion 262. Under such configuration, through rotation of longitudinal member 278, the user can controllably select a rotational position of bore 266 defined in first member 262. In this manner, bore 266 can be selectively chosen to be aligned with port 280 on housing portion 210 to provide fluid communication with port 280. Similarly, bore 266 may be mis-aligned with port 280 to close off port 280 through rotation of rotor 260. For example, bore 266 and longitudinal member 278 may be longitudinally aligned to provide fluid communication with port 280 when longitudinal member 278 is aligned with port 280. Groove 295 may be configured to enable only a partial rotation of rotor 260. As illustrated in FIG. 14, groove 295 extends about 90 degrees around the circumference of the inner surface of neck portion 218. By limiting rotation of rotor 260 to about a 90-degree rotation, the user may conveniently rotate rotor 260 with, for example, a thumb and achieve a single hand actuation. In addition, the user can readily determine whether fluid communication has been established between port 280 and tubular member 250 by determining the position of the longitudinal member 278. For example, longitudinal member 278 may be configured to align with port 280 when bore 266 is in fluid communication with port 280. As mentioned hereinabove, it is further contemplated that rotor 260 may be rotated to an intermediate position in which bore 266 is partially aligned with port 280 providing a fluid communication between port 280 and tubular member 250.

Alternatively, as discussed hereinabove, visual indicia may be provided on an outer surface of outer portion 264. Moreover, first portion 262 of rotor 260 may define additional bores (not shown) to reduce the degree of rotation of longitudinal member 278 to establish fluid communication between bore 266 and port 280. Under such configuration, housing portion 210 may provide a detent mechanism or tactile means (not shown) to indicate to the user the intermediate positions in which the additional bores are aligned with port 280. It is further envisioned that first portion 262 of rotor 260 may define additional bores having various sizes in diameters. In this manner, the user may control the fluid flow and fluid pressure by choosing the desired fluid flow and/or pressure associated with the particular bore. By arranging the bores with gradual increase in the size of the diameter, the user can gradually increase or decrease the fluid flow and fluid pressure into the body cavity. The number of bores and the varying diameter of the bores may be tailored to the application being performed. In this manner, the user may control the flow and pressure of the fluid, as well as establishing or cutting off fluid communication with a single hand. In addition, the snug fit of rotor 260 and the type of material chosen for rotor 260 may also affect the pressure capacity of rotor 260.

In use, cannula 200 is inserted through a small incision made in the skin of a patient or through a natural orifice. At this time bore 266 defined in first portion 262 of rotor 260 is misaligned with port 280, as shown in FIGS. 13. Upon placing a distal end of cannula 200 adjacent the target surgical site, fluid source 400 may be connected to port 280. Optionally, an obturator may be utilized to advance cannula 200 into the tissue and an inflatable dissection balloon may be used to dissect tissue to provide working space. At this time, longitudinal member 278 may be rotated in the direction of arrow "Z," as shown in FIG. 15, causing nub 290 to be rotated about 90 degrees within groove 295, as shown in FIGS. 14 and 16. In this manner, bore 266 defined in first portion 262 of rotor 260 aligns with port 280 to provide fluid communication therebetween. In this manner, insufflation fluid, for example, may be supplied to the body cavity to maintain accessible working space as desired. (Similarly, port 280 may be connected to a vacuum source and provide suction at the surgical site.) Surgical instruments may then be inserted through lumen 212 and longitudinal channel 252 of cannula 200 while maintaining a sealing relationship with seals 222a, 222b. In addition, by utilizing bores of various diameters, the user may control the flow and pressure of the fluid that is supplied to the body cavity.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical access device comprising:
   a housing member defining a lumen therethrough, the housing member including a port in fluid communication with the lumen;
   a tubular member defining a channel therethrough in fluid communication with the lumen of the housing member, the tubular member defining a longitudinal axis;
   a rotor defining a longitudinal passage therethrough and a bore on a sidewall of the rotor, the rotor rotatably associated with the housing member and coupled to the tubular member; and
   a lever translatably mounted on the housing member, wherein axial translation of the lever causes rotation of the rotor about the longitudinal axis between an open position in which the bore is aligned with the port providing a fluid communication between the port and the tubular member and a closed position in which the sidewall of the rotor closes off the port, wherein the lumen of the housing member and the longitudinal passage of the rotor are in communication to receive a surgical instrument therethrough independent of a rotational position of the rotor.

2. The surgical access device according to claim 1, wherein the lever includes first and second members in a substantially superposed relation with each other.

3. The surgical access device according to claim 2, wherein the first member is slidably disposed on an outer surface of the housing member and the second member is slidably disposed on an inner surface of the housing member.

4. The surgical access device according to claim 3, wherein an inner surface of the second member of the lever defines a groove along a length thereof.

5. The surgical access device according to claim 4, wherein the rotor includes a nub radially extending from the sidewall of the rotor, the nub slidably engaging the groove defined in the second member.

6. The surgical access device according to claim 4, wherein the groove of the lever defines an acute angle with respect to the longitudinal axis of the tubular member.

7. The surgical access device according to claim 5, wherein the nub of the rotor is oriented at an angle with respect to the longitudinal axis of the tubular member.

8. The surgical access device according to claim 3, wherein the housing member includes a circumferential ridge radially extending from the inner surface thereof.

9. The surgical access device according to claim 8, wherein the rotor defines a circumferential groove corresponding to the circumferential ridge of the housing member, the circumferential groove rotatably engaging the circumferential ridge.

10. The surgical access device according to claim 2, wherein the first member of the lever conforms to a contour of an outer surface of the housing member.

11. The surgical access device according to claim 2, wherein the second member of the lever conforms to a contour of an outer surface of the rotor.

12. The surgical access device according to claim 1, wherein the port is connected to at least one of a fluid supply or a vacuum source.

13. A surgical access device comprising:
   a cannula including a housing and a tubular member extending from the housing, the housing including a port in communication with the tubular member, the port connected to a fluid supply or a vacuum source, the cannula defining a lumen therethrough; and
   a rotatable hub defining a passage therethrough, the rotatable hub including a first portion rotatably disposed within the housing and defining a bore and a second portion at least partially surrounding the tubular member, the second portion being disposed exterior to the housing of the cannula, wherein rotation of the second portion causes concomitant rotation to the first portion between an open position in which the bore is aligned with the port providing a fluid communication between the port and the tubular member and a closed position in which the first portion closes off the port, wherein the lumen of the cannula and the passage of the rotatable hub are in communication to receive a surgical instrument therethrough independent of a rotational position of the rotatable hub, wherein the port is stationary during transition of the first portion of the rotatable hub between the open and closed positions.

14. The surgical access device according to claim 13, wherein the rotatable hub includes a nub radially extending from an outer surface of the rotatable hub.

15. The surgical access device according to claim 14, wherein the housing defines a partially circumferential groove, the nub of the rotatable hub slidably engaging the partially circumferential groove.

16. The surgical access device of claim 15, wherein the partially circumferential groove defines a 90-degree angle.

17. The surgical access device according to claim 13, wherein the first portion of the rotatable hub defines a circumferential groove.

18. The surgical access device according to claim 17, wherein the housing includes a circumferential ridge radially extending from an inner surface of the housing, the circumferential groove of rotatable hub rotatably engages the circumferential ridge of the housing.

* * * * *